(12) United States Patent
Best

(10) Patent No.: US 12,053,405 B2
(45) Date of Patent: Aug. 6, 2024

(54) ANKLE BRACE DEVICES, SYSTEMS, AND METHODS

(71) Applicant: Shock Doctor, Inc., Fountain Valley, CA (US)

(72) Inventor: Blaze Best, New York, NY (US)

(73) Assignee: Shock Doctor, Inc., Fountain Valley, CA (US)

( * ) Notice: Subject to any disclaimer, the term of this patent is extended or adjusted under 35 U.S.C. 154(b) by 283 days.

(21) Appl. No.: 16/584,075

(22) Filed: Sep. 26, 2019

(65) Prior Publication Data

US 2020/0100929 A1 Apr. 2, 2020

Related U.S. Application Data

(60) Provisional application No. 62/737,462, filed on Sep. 27, 2018.

(51) Int. Cl.
*A61F 5/01* (2006.01)

(52) U.S. Cl.
CPC .................... *A61F 5/0111* (2013.01)

(58) Field of Classification Search
CPC .... A61F 5/0111; A61F 5/0127; A61F 13/064; A61F 13/065; A61F 13/066; A61F 5/01; A61F 5/0104
USPC ............ 602/27, 23, 5, 12; 128/882
See application file for complete search history.

(56) References Cited

U.S. PATENT DOCUMENTS

| | | |
|---|---|---|
| 2,590,648 A | 3/1952 | Pitz |
| 2,994,322 A | 8/1961 | Cullen et al. |
| 3,298,365 A | 1/1967 | Lewis |
| 3,674,023 A * | 7/1972 | Mann ............... A61F 13/066 602/65 |
| 4,523,394 A | 6/1985 | Lindh et al. |

(Continued)

FOREIGN PATENT DOCUMENTS

| | | |
|---|---|---|
| DE | 8522310 U1 | 9/1985 |
| DE | 102006041195 A1 | 3/2008 |

(Continued)

OTHER PUBLICATIONS

International Preliminary Report on Patentability received for PCT Patent Application No. PCT/US2013/060152, mailed on Mar. 26, 2015, 7 pages.
International Preliminary Report on Patentability received for PCT Patent Application No. PCT/US2016/035853, mailed on Dec. 13, 2018, 11 pages.

(Continued)

*Primary Examiner* — Caitlin A Carreiro
(74) *Attorney, Agent, or Firm* — FAEGRE DRINKER BIDDLE & REATH LLP

(57) ABSTRACT

An ankle brace includes a main body that is configured to receive a foot of a wearer. The main body has a first side portion and a second side portion opposite the first side portion. An adjustable stirrup assembly is coupled to the main body. The adjustable stirrup assembly includes an inner stirrup and an outer stirrup. The inner stirrup is configured to underlie the sole of the foot of the wearer. The inner stirrup includes a first inner stirrup strap and a second inner stirrup strap. The first inner stirrup strap is coupled to the first side portion of the main body. The second inner stirrup strap is coupled to the second side portion of the main body, and the second inner stirrup strap detachably couples to the first inner stirrup strap. The outer stirrup at least partially underlies the inner stirrup.

14 Claims, 15 Drawing Sheets

(56) References Cited

U.S. PATENT DOCUMENTS

| | | | |
|---|---|---|---|
| RE33,395 E | 10/1990 | Peters | |
| 4,977,891 A | 12/1990 | Grim | |
| 5,000,195 A * | 3/1991 | Neal | A61F 5/0111 602/27 |
| 5,031,607 A | 7/1991 | Peters | |
| 5,067,486 A | 11/1991 | Hely | |
| 5,090,404 A | 2/1992 | Kallassy | |
| 5,209,722 A | 5/1993 | Miklaus et al. | |
| 5,366,439 A | 11/1994 | Peters | |
| 5,429,588 A | 7/1995 | Young et al. | |
| 5,445,602 A | 8/1995 | Grim et al. | |
| 5,454,382 A | 10/1995 | Tariah et al. | |
| 5,496,263 A | 3/1996 | Fuller et al. | |
| 5,501,659 A | 3/1996 | Morris et al. | |
| 5,507,720 A | 4/1996 | Lampropoulos | |
| 5,527,269 A | 6/1996 | Reithofer | |
| 5,630,792 A | 5/1997 | Neal | |
| 5,676,642 A | 10/1997 | Peters | |
| D391,640 S | 3/1998 | Oviedo, Jr. | |
| 5,741,222 A | 4/1998 | Fiore | |
| 5,759,168 A | 6/1998 | Bussell et al. | |
| 5,795,316 A | 8/1998 | Gaylord | |
| 5,797,865 A | 8/1998 | Mcdavid, III | |
| 5,836,903 A | 11/1998 | Peters | |
| 5,897,520 A | 4/1999 | Gerig | |
| 5,902,259 A | 5/1999 | Wilkerson | |
| 5,944,678 A | 8/1999 | Hubbard | |
| 5,951,504 A | 9/1999 | Iglesias et al. | |
| 5,966,843 A | 10/1999 | Sand et al. | |
| 5,971,946 A | 10/1999 | Quinn et al. | |
| 5,980,474 A * | 11/1999 | Darcey | A61F 5/0111 602/8 |
| D418,259 S | 12/1999 | Morton | |
| 6,053,884 A | 4/2000 | Peters | |
| 6,146,350 A | 11/2000 | Morton | |
| D436,177 S | 1/2001 | Miller | |
| 6,270,468 B1 | 8/2001 | Townsend et al. | |
| 6,272,772 B1 | 8/2001 | Sherman | |
| 6,299,587 B1 | 10/2001 | Birmingham | |
| 6,524,266 B1 | 2/2003 | Peters | |
| 6,602,215 B1 * | 8/2003 | Richie, Jr. | A61F 5/05 128/882 |
| 6,656,145 B1 | 12/2003 | Morton | |
| 6,739,077 B2 | 5/2004 | Morgan | |
| 6,749,578 B2 | 6/2004 | Peters | |
| 6,767,332 B1 | 7/2004 | Pardue et al. | |
| 6,772,541 B1 | 8/2004 | Ritter et al. | |
| 6,792,700 B2 | 9/2004 | Gallegos | |
| 6,858,017 B2 | 2/2005 | Peters | |
| 7,014,621 B2 | 3/2006 | Nelson | |
| 7,020,989 B2 | 4/2006 | Kim | |
| 7,081,102 B1 | 7/2006 | Koetter et al. | |
| 7,267,656 B2 | 9/2007 | Cooper | |
| D552,743 S | 10/2007 | Verkade et al. | |
| RE40,215 E | 4/2008 | Cummings et al. | |
| 7,364,561 B1 | 4/2008 | Morton | |
| 7,370,442 B2 | 5/2008 | Jung et al. | |
| 7,429,254 B1 | 9/2008 | Engelman | |
| 7,587,841 B2 | 9/2009 | Culpepper | |
| 7,615,026 B1 | 11/2009 | Peters et al. | |
| 7,713,224 B1 | 5/2010 | Peters et al. | |
| D618,359 S | 6/2010 | Einarsson | |
| D620,124 S | 7/2010 | Einarsson | |
| 7,753,865 B1 * | 7/2010 | Hely | A61F 5/0111 128/882 |
| 7,785,283 B1 | 8/2010 | Bledsoe | |
| 7,828,758 B2 | 11/2010 | Clements et al. | |
| 8,007,454 B1 * | 8/2011 | Zerr | A61F 5/0111 602/23 |
| D663,852 S | 7/2012 | Joseph | |
| D672,878 S | 12/2012 | Einarsson | |
| D673,280 S | 12/2012 | Einarsson | |
| D696,409 S | 12/2013 | Best et al. | |
| 8,734,371 B2 | 5/2014 | Robertson | |
| D708,344 S | 7/2014 | Best et al. | |
| 2001/0015023 A1 | 8/2001 | Funk | |
| 2001/0054240 A1 | 12/2001 | Bordin et al. | |
| 2001/0056251 A1 | 12/2001 | Peters | |
| 2002/0038522 A1 | 4/2002 | Houser et al. | |
| 2002/0055696 A1 | 5/2002 | Borsoi | |
| 2002/0062579 A1 | 5/2002 | Caeran | |
| 2003/0014001 A1 | 1/2003 | Martin | |
| 2003/0154627 A1 | 8/2003 | Hirayama | |
| 2003/0213150 A1 | 11/2003 | Caeran | |
| 2003/0233770 A1 | 12/2003 | Foscaro | |
| 2004/0019309 A1 | 1/2004 | Nelson et al. | |
| 2004/0049951 A1 | 3/2004 | Chen | |
| 2004/0084390 A1 | 5/2004 | Bernstein | |
| 2004/0111049 A1 | 6/2004 | Nelson | |
| 2004/0167453 A1 | 8/2004 | Peters | |
| 2004/0172854 A1 | 9/2004 | Delgorgue et al. | |
| 2004/0236259 A1 | 11/2004 | Pressman et al. | |
| 2004/0250452 A1 | 12/2004 | Farys | |
| 2005/0070833 A1 | 3/2005 | Shields | |
| 2005/0085755 A1 * | 4/2005 | Rabe | A61F 5/0111 602/27 |
| 2005/0171461 A1 | 8/2005 | Pick | |
| 2005/0177083 A1 | 8/2005 | Heil | |
| 2005/0178028 A1 | 8/2005 | Light | |
| 2005/0204585 A1 | 9/2005 | Loveridge et al. | |
| 2005/0217147 A1 | 10/2005 | Dion | |
| 2005/0222531 A1 | 10/2005 | Moore | |
| 2005/0236784 A1 | 10/2005 | Zampieri et al. | |
| 2006/0005432 A1 | 1/2006 | Kassai et al. | |
| 2006/0032090 A1 | 2/2006 | Chen et al. | |
| 2006/0059719 A1 | 3/2006 | Lebo | |
| 2006/0084899 A1 | 4/2006 | Verkade et al. | |
| 2007/0027420 A1 | 2/2007 | Yu | |
| 2007/0049855 A1 | 3/2007 | Mattear | |
| 2007/0056189 A1 | 3/2007 | Schafer Mathison | |
| 2007/0113427 A1 | 5/2007 | Mansfield | |
| 2008/0010860 A1 | 1/2008 | Gyr | |
| 2008/0120871 A1 | 5/2008 | Sato et al. | |
| 2008/0263897 A1 | 10/2008 | Shepherd et al. | |
| 2009/0031585 A1 | 2/2009 | Shepherd et al. | |
| 2009/0044427 A1 | 2/2009 | Shepherd et al. | |
| 2009/0084390 A1 | 4/2009 | Davis et al. | |
| 2009/0105704 A1 | 4/2009 | Gordon, Jr. | |
| 2009/0165333 A1 | 7/2009 | Litchfield et al. | |
| 2009/0216167 A1 | 8/2009 | Harris | |
| 2009/0247920 A1 | 10/2009 | Clements et al. | |
| 2010/0011620 A1 | 1/2010 | Nakano | |
| 2010/0036306 A1 | 2/2010 | Lussier et al. | |
| 2010/0137770 A1 | 6/2010 | Ingimundarson et al. | |
| 2011/0028877 A1 | 2/2011 | Vollbrecht et al. | |
| 2011/0035967 A1 | 2/2011 | Shmueli | |
| 2011/0179673 A1 | 7/2011 | Bisson et al. | |
| 2013/0204172 A1 | 8/2013 | Mehweg et al. | |
| 2014/0230278 A1 | 8/2014 | Schafer Mathison | |
| 2015/0173930 A1 | 6/2015 | Maloney | |
| 2015/0216702 A1 | 8/2015 | Best et al. | |
| 2015/0265449 A1 | 9/2015 | Togninalli et al. | |
| 2015/0374527 A1 | 12/2015 | Wenger | |
| 2016/0030222 A1 | 2/2016 | Collier et al. | |
| 2016/0157551 A1 | 6/2016 | Goldberg | |
| 2018/0042751 A1 | 2/2018 | Derose | |
| 2018/0235312 A1 | 8/2018 | Hanft | |
| 2019/0099282 A1 | 4/2019 | Best et al. | |
| 2020/0100928 A1 | 4/2020 | Best et al. | |

FOREIGN PATENT DOCUMENTS

| | | |
|---|---|---|
| EP | 0416913 A2 | 3/1991 |
| EP | 0744906 A1 | 12/1996 |
| EP | 1152720 A1 | 11/2001 |
| EP | 1234560 A1 | 8/2002 |
| EP | 1346710 A1 | 9/2003 |
| EP | 1928369 A2 | 6/2008 |
| EP | 2050429 A1 | 4/2009 |
| EP | 2379020 A1 | 10/2011 |
| JP | 6364574 B1 | 7/2018 |
| WO | 91/12781 A1 | 9/1991 |
| WO | 95/22264 A1 | 8/1995 |

(56) References Cited

FOREIGN PATENT DOCUMENTS

| WO | 97/36507 | A1 | 10/1997 |
|---|---|---|---|
| WO | 00/40202 | A2 | 7/2000 |
| WO | 00/48537 | A1 | 8/2000 |
| WO | 2004/009001 | A1 | 1/2004 |
| WO | 2004/098467 | A1 | 11/2004 |
| WO | 2004/108026 | A1 | 12/2004 |
| WO | 2006/061603 | A2 | 6/2006 |
| WO | 2007/041345 | A2 | 4/2007 |
| WO | 2007/078845 | A2 | 7/2007 |
| WO | 2008/028643 | A1 | 3/2008 |
| WO | 2009/023094 | A2 | 2/2009 |
| WO | 2009/090259 | A1 | 7/2009 |
| WO | 2010/065097 | A1 | 6/2010 |
| WO | 2014/043695 | A1 | 3/2014 |
| WO | 2017/209770 | A1 | 12/2017 |
| WO | 2020/069149 | A1 | 4/2020 |
| WO | 2020/069151 | A1 | 4/2020 |

OTHER PUBLICATIONS

International Search Report and Written Opinion received for PCT Patent Application No. PCT/US2013/060152, mailed on Jan. 3, 2014, 8 pages.
International Search Report and Written Opinion received for PCT Patent Application No. PCT/US2016/035853, mailed on Mar. 21, 2017, 15 pages.
International Search Report and Written Opinion received for PCT Patent Application No. PCT/US2019/053182, mailed on Feb. 20, 2020, 15 pages.
International Search Report and Written Opinion received for PCT Patent Application No. PCT/US2019/053185, mailed on Feb. 4, 2020, 14 pages.
Parlial Supplementary European Search Report issued in EP Application No. EP13837423.6, mailed Apr. 21, 2016, 7 pages.
Supplemental EP Search Report issued in EP Application No. 13837423.6 mailed Jul. 28, 2016, 11 pages.

* cited by examiner

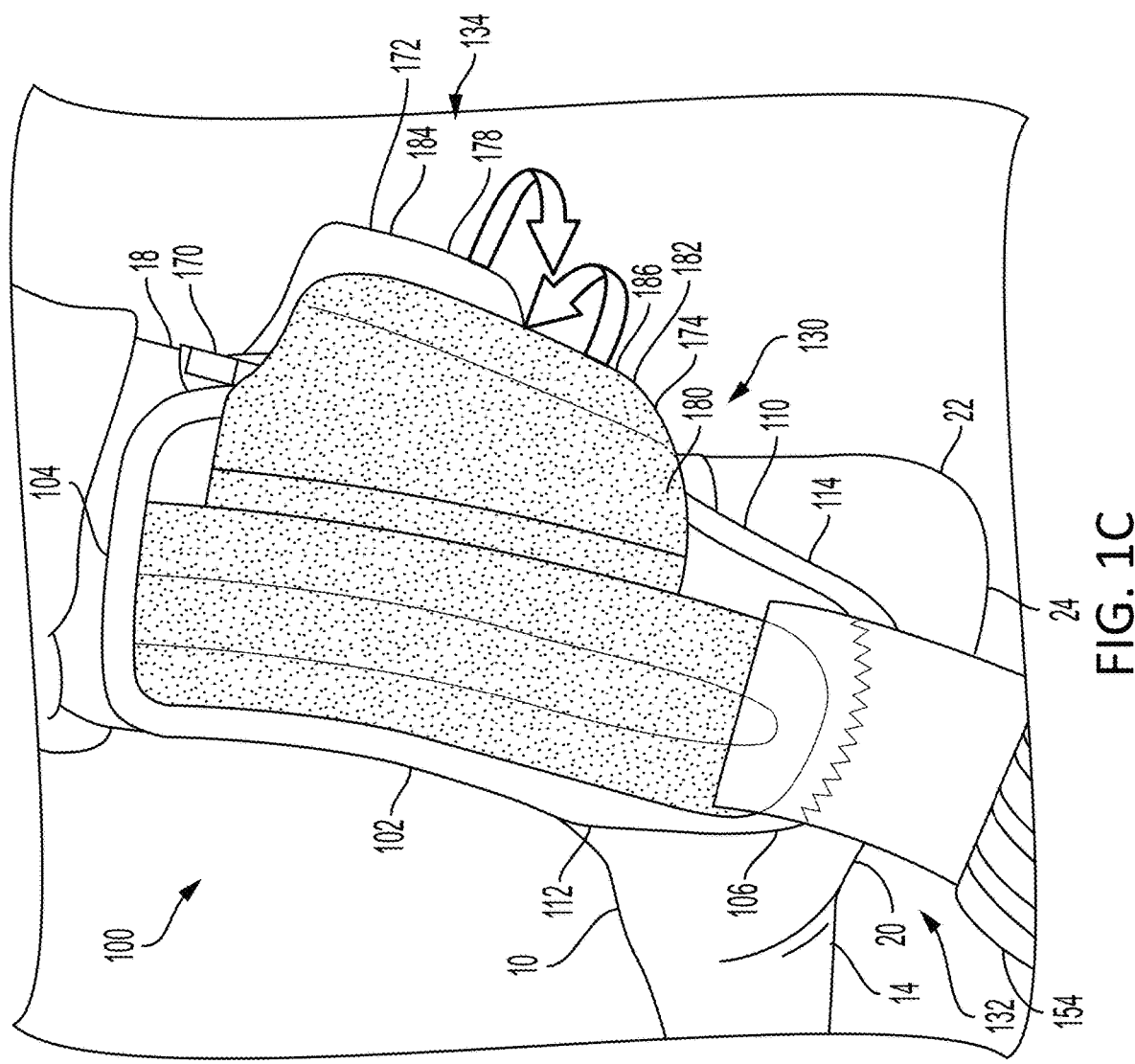

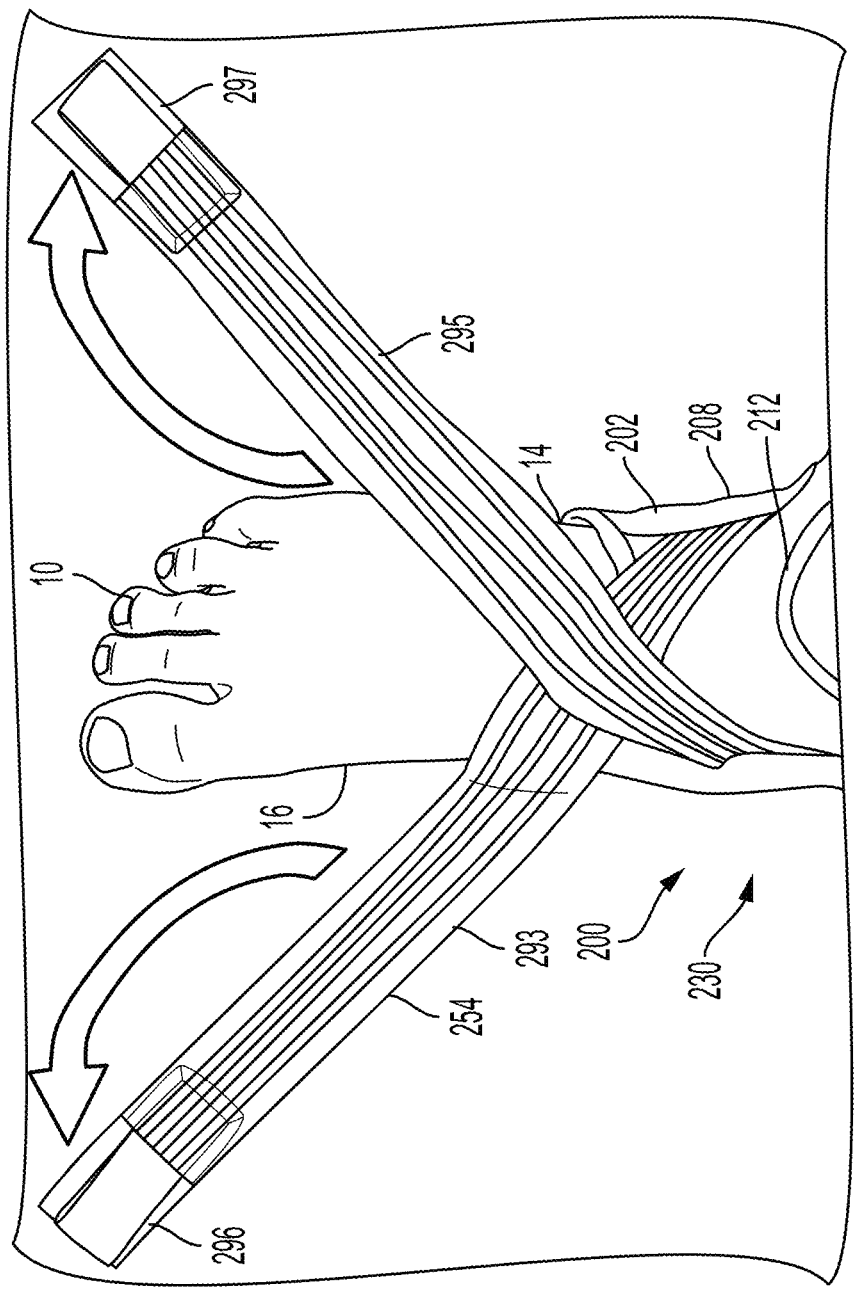

ANKLE BRACE DEVICES, SYSTEMS, AND METHODS

CROSS REFERENCE TO RELATED APPLICATION

The present application claims the benefit of and priority to, under 35 U.S.C. § 119(e), U.S. Provisional Application Ser. No. 62/737,462, filed on Sep. 27, 2018, which is hereby incorporated herein by reference in its entirety for all that it teaches and for all purposes.

TECHNICAL FIELD

The present disclosure relates generally to protective and supportive athletic gear and methods of making the same. The present disclosure relates to devices and methods of supporting a wearer's ankle, such as ankle straps and ankle braces. More particularly, the present disclosure relates to ankle braces having ankle stays for providing medial/lateral ankle support.

BACKGROUND

Each year, many people, both athletes and non-athletes, suffer ankle injuries. In some cases, athletes wrap their ankles with adhesive tape in an attempt to prevent ankle injuries and/or to support their ankles after an injury has occurred. In many instances, athletes and others use ankle braces to protect and/or to rehabilitate their ankles.

Devices for supporting or stabilizing the foot or ankle of a wearer may be worn by a wearer for everyday use and/or for use when engaging in physical activity. Injuries to the foot or ankle are common and may affect a wearer's physical ability and/or athletic performance. For certain wearers it may be beneficial to use an artificial structure to support a foot or ankle that has been weakened or injured. Certain rigid structures may be worn through the day and/or when engaging in sports to provide structural support, or prevent further injury. Often a physician or healthcare worker may apply a custom fitted support or structure to the outside of wearer's limb to provide weight bearing support to the wearer's limb.

While a variety of ankle braces are known, there is a desire for continued improvement in the performance and comfort of known ankle braces. Certain support structures for the foot or ankle of a wearer, such as straps or braces, are available and may provide certain advantages such as agility, comfort, or weight bearing capabilities. However, certain options may be unsuitable because of particular characteristics. For example, sleeves that are currently available may be flexible or comfortable, but may not provide adequate support. In other instances, a custom fitted device may be costly and/or require extensive customization for a wearer. Additionally, certain devices that provide structural support may be uncomfortable, or unsuited for use in certain sports that require a particular level of agility or movement by the wearer's limbs. There is thus a need for a device or method for supporting a limb or limbs of a wearer that provides suitable weight bearing capability yet is flexible and comfortable enough to be used during sports and is also cost effective and accessible.

SUMMARY

In a first example, an ankle brace according to the present disclosure includes a main body that is configured to receive a foot of a wearer. The main body has a first side portion and a second side portion opposite the first side portion. An adjustable stirrup assembly is coupled to the main body. The adjustable stirrup assembly includes an inner stirrup and an outer stirrup. The inner stirrup is configured to underlie the sole of the foot of the wearer. The inner stirrup includes a first inner stirrup strap and a second inner stirrup strap. The first inner stirrup strap is coupled to the first side portion of the main body. The second inner stirrup strap is coupled to the second side portion of the main body, and the second inner stirrup strap detachably couples to the first inner stirrup strap. The outer stirrup at least partially underlies the inner stirrup.

In a second example, the ankle brace of the first example, wherein the first inner stirrup strap includes a first end portion that is fixedly coupled to the first side portion of the main body and a second end portion, the second inner stirrup strap includes a first end portion that is fixedly coupled to the second side portion of the main body and a second end portion, and the second end portion of the second inner stirrup strap detachably couples to the second end portion of the first inner stirrup strap.

In a third example, the ankle brace of the first example or the second example, wherein the outer stirrup at least partially underlies both of the first inner stirrup strap and the second inner stirrup strap.

In a fourth example, the ankle brace of the first example through the third example, wherein the first inner stirrup strap and the second inner stirrup strap are configured to detachably couple to each other under the sole of the foot of the wearer.

In a fifth example, the ankle brace of the first example through the fourth example, further including a plurality of loops carried by the first inner stirrup strap; and a plurality of hooks carried by the second inner stirrup strap, the plurality of hooks detachably coupling to the plurality of loops to detachably couple the second inner stirrup strap to the first inner stirrup strap.

In a sixth example, the ankle brace of the first example through the fifth example, wherein the outer stirrup includes a first crossing outer stirrup strap that detachably couples to the first side portion of the main body and a second crossing outer stirrup strap that detachably couples to the second side portion of the main body.

In a seventh example, the ankle brace of the first example through the sixth example, further including an adjustable securement assembly coupled to the main body, the adjustable securement assembly including: a first securement strap coupled to the first side portion of the main body; and a second securement strap coupled to the second side portion of the main body, the second securement strap detachably coupling to the first securement strap.

In an eighth example, the ankle brace of the first example through the seventh example, wherein the adjustable securement assembly further includes a bridge coupled to the first side portion of the main body and the second side portion of the main body, the bridge being configured to be disposed between the leg of the wearer and the first securement strap and the second securement strap.

In a ninth example, the ankle brace of the first example through the eighth example, wherein the adjustable securement assembly further includes a first upper wrapping strap.

In a tenth example, the ankle brace of the first example through the ninth example, wherein the adjustable securement assembly further includes a second upper wrapping strap, the second upper wrapping strap being detachably coupled to the first upper wrapping strap.

In an eleventh example, an ankle brace according to the present disclosure includes a main body that is configured to receive a foot of a wearer. The main body has a first side portion and a second side portion opposite the first side portion. The ankle brace further includes a stirrup coupled to the main body and configured to underlie the sole of the foot of the wearer. The stirrup includes a first stirrup strap coupled to the first side portion of the main body and a second stirrup strap coupled to the second side portion of the main body. The second stirrup strap detachably couples to the first stirrup strap. An adjustable securement assembly is coupled to the main body. The adjustable securement assembly includes a first securement strap and a second securement strap. The first securement strap is coupled to the first side portion of the main body and the second securement strap coupled to the second side portion of the main body. The second securement strap detachably couples to the first securement strap.

In a twelfth example, the ankle brace of the eleventh example, wherein the adjustable securement assembly further includes a bridge coupled to the first side portion of the main body and the second side portion of the main body. The bridge is configured to be disposed between the leg of the wearer and the first securement strap and the second securement strap.

In a thirteenth example, the ankle brace of the eleventh example or the twelfth example, further including a plurality of hooks carried by the first securement strap and a plurality of loops carried by the second securement strap. The plurality of loops detachably couple to the plurality of hooks to detachably couple the second securement strap to the first securement strap.

In a fourteenth example, the ankle brace of the eleventh example through the thirteenth example, wherein the first inner stirrup strap includes a first end portion fixedly coupled to the first side portion of the main body and a second end portion, the second inner stirrup strap includes a first end portion fixedly coupled to the second side portion of the main body and a second end portion, and the second end portion of the second inner stirrup strap detachably couples to the second end portion of the first inner stirrup strap.

In a fifteenth example, the ankle brace of the eleventh example through the fourteenth example, wherein the first inner stirrup strap and the second inner stirrup strap are configured to detachably couple to each other under the sole of the foot of the wearer.

In a sixteenth example, the ankle brace of the eleventh example through the fifteenth example, further including a plurality of hooks carried by the first inner stirrup strap; and a plurality of loops carried by the second inner stirrup strap, the plurality of loops detachably coupling to the plurality of hooks to detachably couple the second inner stirrup strap to the first inner stirrup strap.

In a seventeenth example, the ankle brace of the eleventh example through the sixteenth example, wherein the adjustable securement assembly further includes an upper wrapping strap.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1C is a side perspective view of the ankle brace of FIG. 1A being secured to the foot of the wearer.

FIG. 2E is a top perspective view of the ankle brace of FIG. 2A being secured to the foot of the wearer.

Figure 1A:
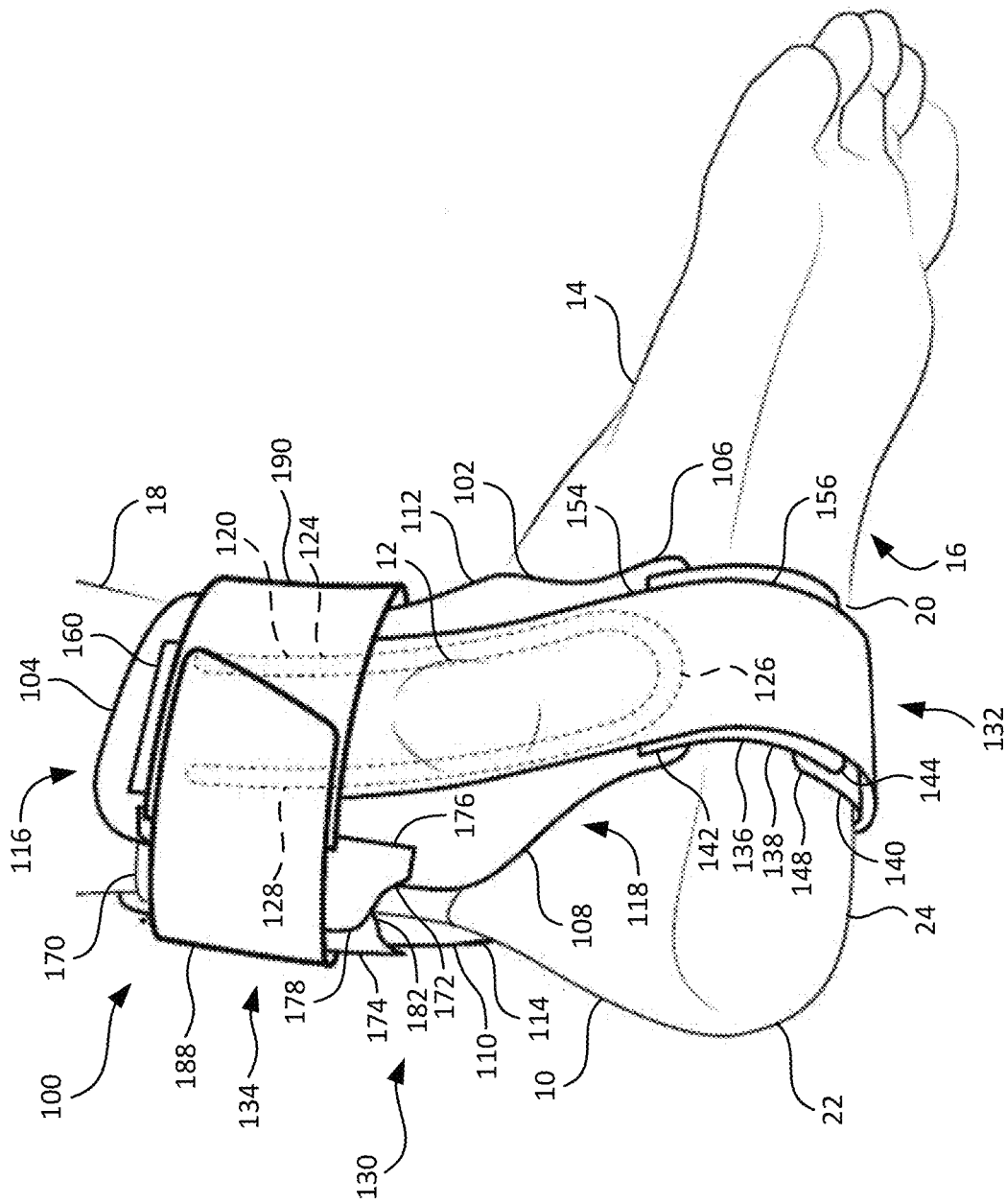
FIG. 1A is a side perspective view of an ankle brace according to an embodiment of the present disclosure being worn on a foot of a wearer.

It should be understood that the drawings are intended facilitate understanding of exemplary embodiments of the present invention are not necessarily to scale.

DETAILED DESCRIPTION

The following description refers to the accompanying drawings which show specific embodiments. Although specific embodiments are shown and described, it is to be understood that additional or alternative features are employed in other embodiments. The following detailed description is not to be taken in a limiting sense, and the scope of the claimed invention is defined by the appended claims and their equivalents.

It should be understood that like reference numerals are intended to identify the same structural components, elements, portions, or surfaces consistently throughout the several drawing figures, as such components, elements, portions, or surfaces may be further described or explained by the entire written specification, of which this detailed description is an integral part. Unless otherwise indicated, the drawings are intended to be read (for example, cross-hatching, arrangement of parts, proportion, degree, etc.) together with the specification, and are to be considered a portion of the written description.

As used herein, "medial" refers generally to a location toward the middle, midline, or median plane of a wearer's body. As used herein, "lateral" refers generally to a location toward the side or outside of a wearer's body. That is the medial side of a wearer's foot is the side that faces inward, generally toward the center of the body and the opposite leg. The lateral side of a wearer's foot is the side that faces outward, generally away from the wearer's body and the opposite foot. Thus the medial side of a wearer's right foot is on the left side of the foot, and the lateral side of a wearer's right foot is on the right side of the foot. The medial side of a wearer's left foot is on the right side of the foot, and the lateral side of a wearer's left foot is on the left side of the foot. As used herein, "anterior" refers generally to a location toward the front of a wearer's body. As used herein, "posterior" refers generally to a location toward the rear of a wearer's body. As used herein, "superior" refers generally to a location toward the top of a wearer's body. As used herein, "inferior" refers generally to a location near the bottom of a wearer's body. As used herein, "sagittal" refers generally to a vertical plane that divides a wearer's body into a left side and a right side, or a vertical plane that divides a wearer's foot into a medial side and transverse side. As used herein, "coronal" refers generally to a vertical plane that divides a wearer's body into an anterior side and a posterior side, or a vertical plane that divides a wearer's foot into an anterior side and a posterior side.

Figure 1B:
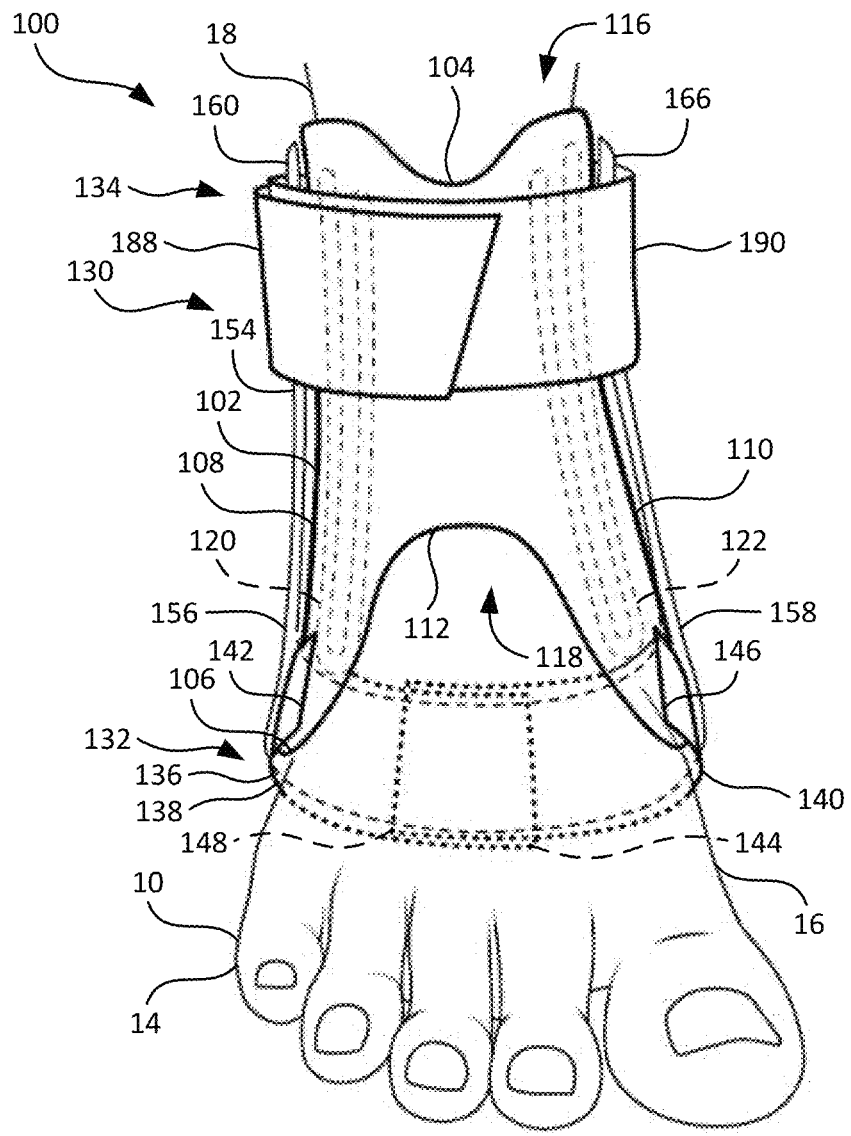
FIG. 1B is a front perspective view of the ankle brace of FIG. 1A being worn on the foot of the wearer.
Figure 1D:
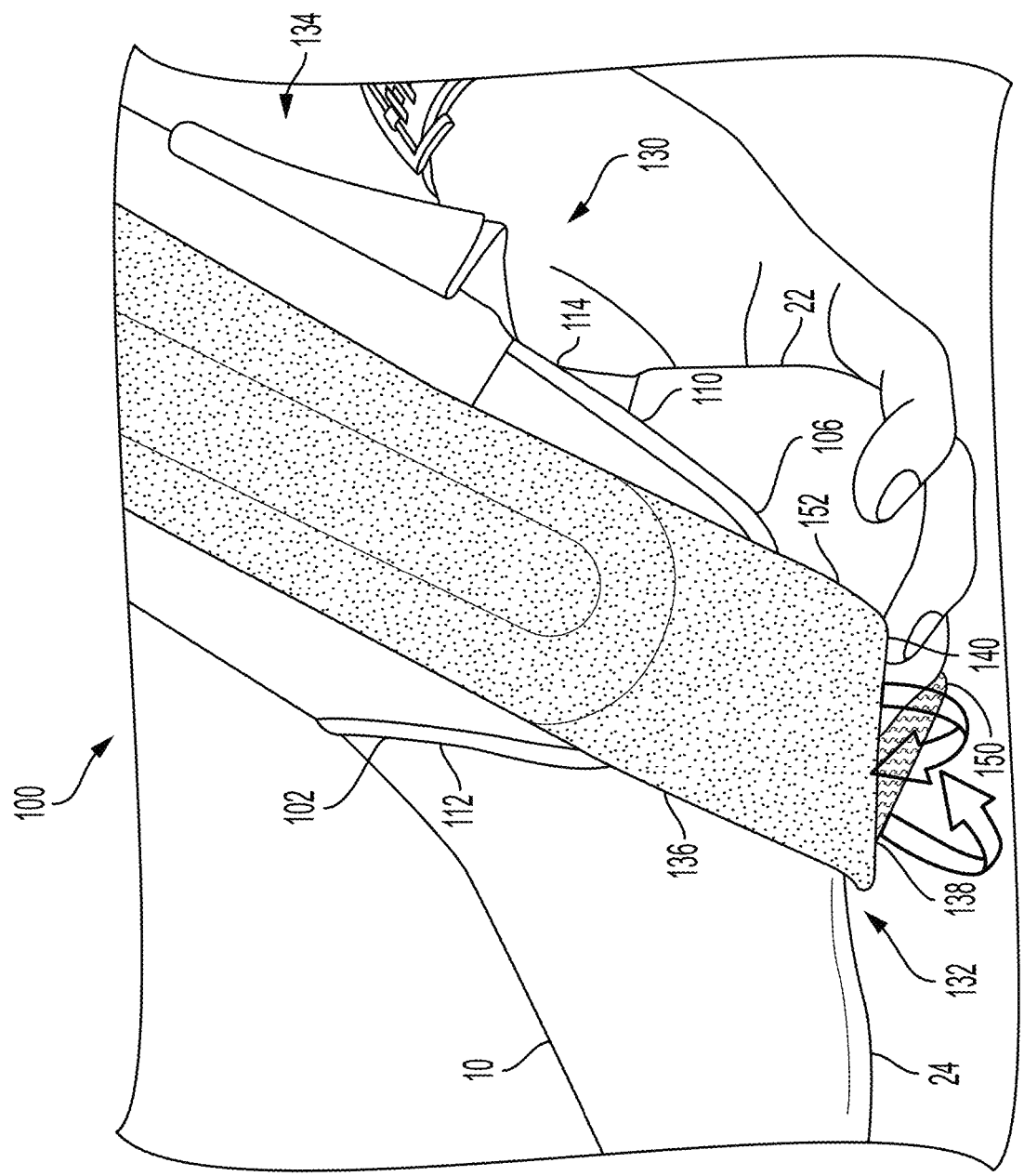
FIG. 1D is another side perspective view of the ankle brace of FIG. 1A being secured to the foot of the wearer.
Figure 1E:
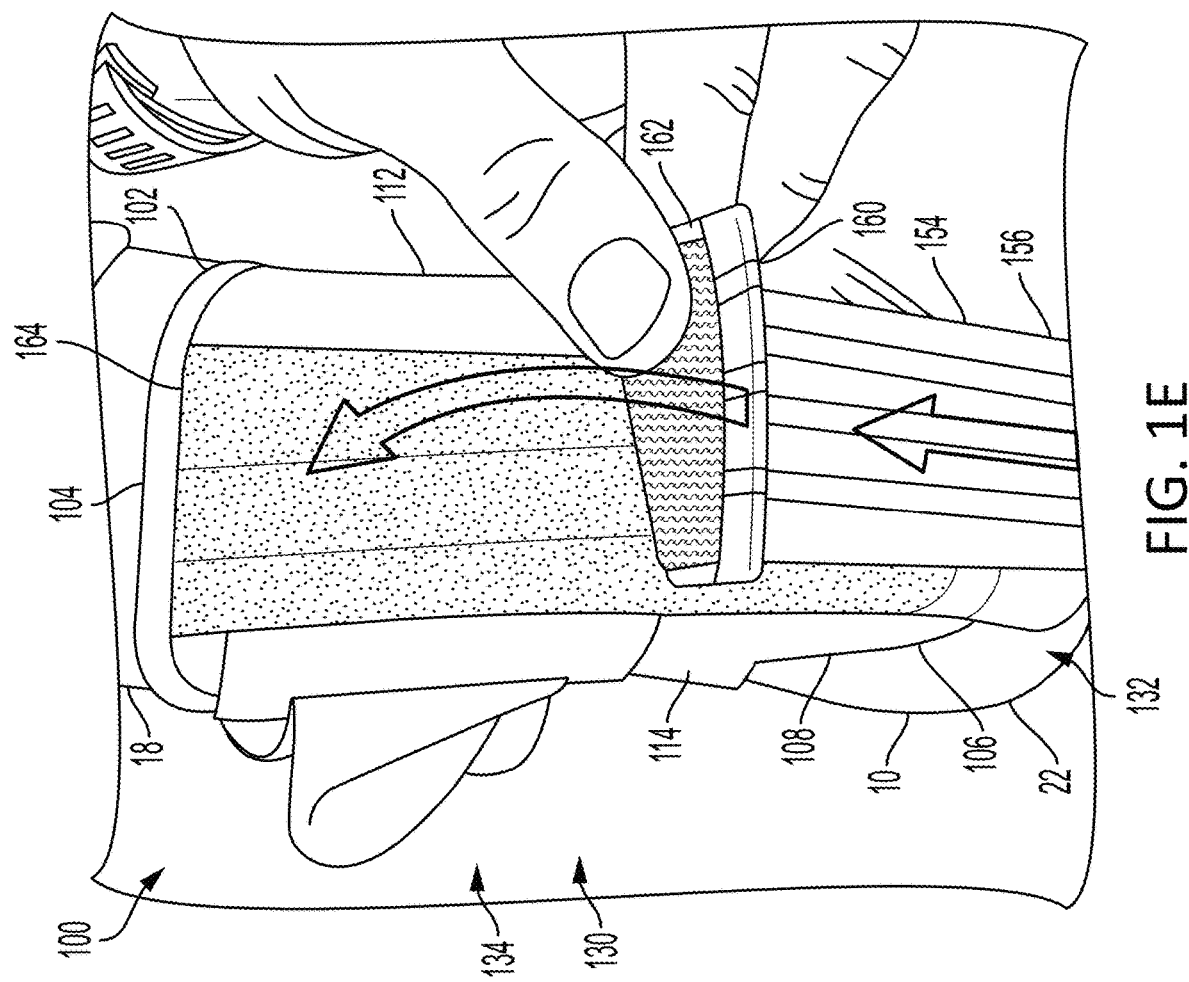
FIG. 1E is another side perspective view of the ankle brace of FIG. 1A being secured to the foot of the wearer.
Figure 1F:
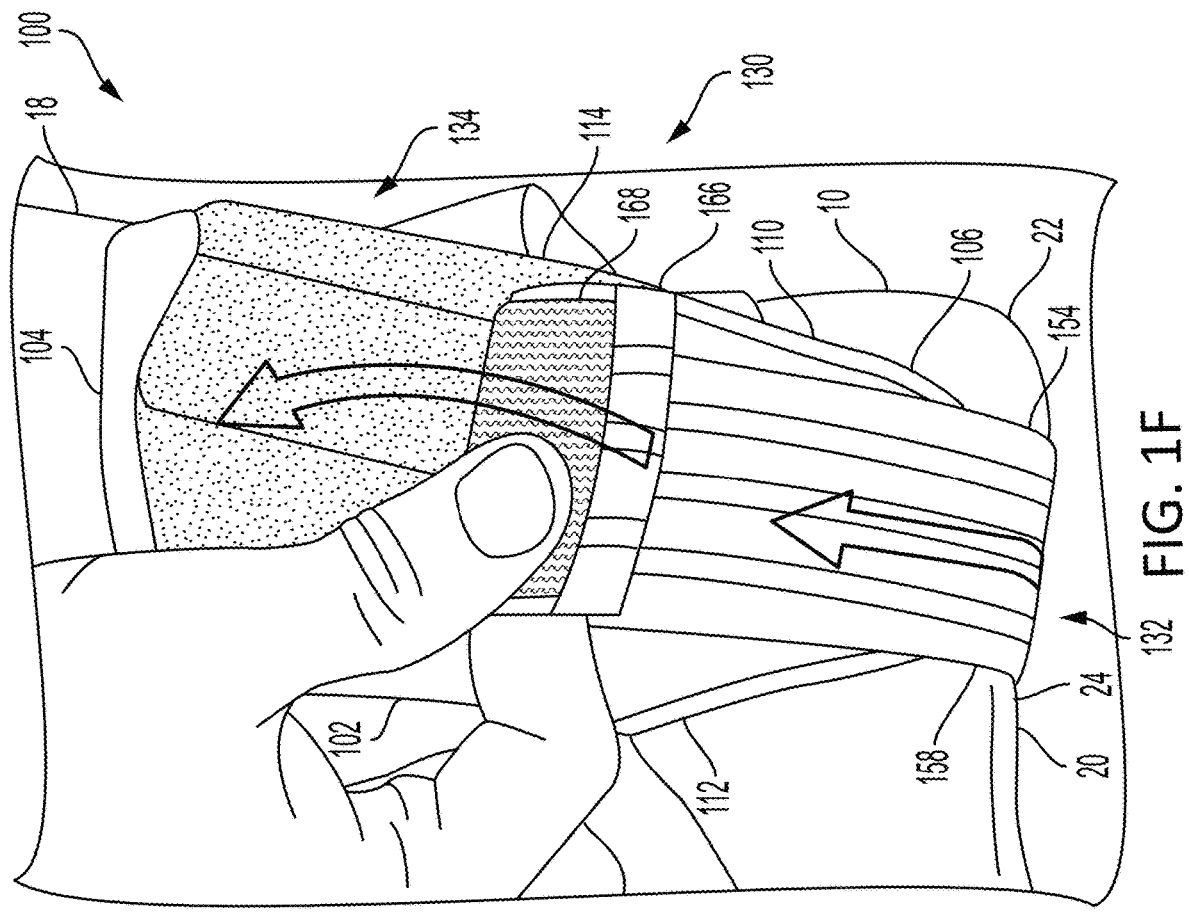
FIG. 1F is yet another side perspective view of the ankle brace of FIG. 1A being secured to the foot of the wearer.

FIGS. 1A and 1B illustrate an ankle brace 100 according to an embodiment of the present disclosure being worn on the foot 10 of a wearer. FIGS. 1C-1G illustrate the ankle brace 100 being secured to the foot 10 of the wearer. The ankle brace 100 includes a main body 102 that is configured to receive the foot 10 of the wearer, including the ankle 12. The main body 102 includes a top portion 104, a first side portion 108, a second side portion 110, a front portion 112, and a rear portion 114. In some embodiments, the top portion 104 is located generally on and against the calf 18 of the wearer when worn. In some embodiments, the first side portion 108 is located generally on and against the lateral side 14 of the wearer's foot 10 when worn (that is, the first side portion 108 may be a lateral side configured to be disposed on the lateral side 14 of the foot 10 of the wearer). In some embodiments, the second side portion 110 is located generally on and against the medial side 16 of a wearer's foot 10 when worn (that is, the second side portion 110 may be a medial side configured to be disposed on the medial side 16 of the foot 10 of the wearer). In some embodiments, the front portion 112 is located generally on and against the front of the calf 18 of the wearer when worn. In some embodiments, the rear portion 114 is located generally on and against the rear of the calf 18 when worn. In some embodiments, the ankle brace 100 is selectively wearable on the right foot or the left foot of the wearer, and/or the ankle brace 100 is symmetric over a sagittal plane bisecting the foot 10 of the wearer.

The top portion 104 of the main body 102 defines a top opening 116 through which the calf 18 of the wearer extends when worn. The bottom portion 106 of the main body 102 defines a bottom opening 118 through which the midfoot 20 and the heel 22 of the foot 10 extend when worn.

The main body 102 may be formed of one or more layers (not shown), each of which may be formed of one or more materials. That is, in some embodiments, the main body 102 is formed of a single layer. In some embodiments, the main body 102 is formed from a plurality of layers. In some embodiments, the plurality of layers of the main body 102 may be coupled to each other via stitching, adhesive, combinations thereof, and the like. In some embodiments, one or more layers of the main body 102 are formed from one or more materials that are resilient yet elastic to support the wearer's foot 10 and allow a wearer to move without restraint. In some embodiments, one or more layers of the main body 102 are formed of fabrics, polymers, composites thereof, and the like. For example, one or more layers of the main body 102 may be formed of neoprene, nylon, polyester, rubber, and latex.

Referring specifically to FIG. 1B, the main body 102 of the ankle brace 100 carries a first ankle support 120, also referred to as a first ankle stay 120, and a second ankle support 122, also referred to as a second ankle stay 122. In some embodiments, the first ankle stay 120 is disposed at the lateral side portion 108 of the main body 102 (that is, the first ankle stay 120 may be a lateral ankle stay configured to be disposed on the lateral side 14 of the foot 10 of the wearer). In some embodiments, the second ankle stay 122 is disposed at the medial side portion 110 of the main body 102 (that is, the second ankle stay 122 may be a medial ankle stay configured to be disposed on the medial side 16 of the foot 10 of the wearer). In some embodiments, the first ankle stay 120 and the second ankle stay 122 are disposed between layers of the main body 102 and coupled to one or more layers of the main body 102 via adhesives (not shown), stitching (not shown) adjacent to the perimeters of the first ankle stay 120 and the second ankle stay 122, or the like.

The ankle stays 120, 122 are monolithic components, although in other embodiments the ankle stays 120, 122 may be formed as separate sections that are joined, for example, via adhesives, ultrasonic welding, or the like. The ankle stays 120, 122 have substantially uniform thicknesses (for example, about 1.5 mm) and widths, although in other embodiments the ankle stays 120, 122 may have non-uniform thicknesses and/or widths. In some embodiments, the ankle stays 120, 122 are formed of polymers (for example, polyethelene), composites (for example, metal reinforced polyethylene), and the like.

Referring specifically to FIG. 1A, the first ankle stay 120 illustratively includes an elongated anterior portion 124, an arcuate inferior portion 126, and an elongated posterior portion 128. The anterior portion 124 is configured to be disposed anteriorly relative to the ankle 12 of the wearer. The inferior portion 126 is configured to be disposed inferiorly relative to the ankle 12 of the wearer. The posterior portion 128 is configured to be disposed posteriorly relative to the ankle 12 of the wearer. The second ankle stay 122 may have the same general shape as the first ankle stay 120. In other embodiments, the first ankle stay 120 and/or the second ankle stay 122 may take different forms. For example, the first ankle stay 120 and/or the second ankle stay 122 may have the shape of any of the ankle stays described and/or shown in U.S. Patent Application Ser. No. 62/737,356, filed Sep. 27, 2018, entitled "ANKLE BRACE DEVICES, SYSTEMS, AND METHODS," the disclosure of which is hereby incorporated by reference. In other embodiments, the ankle brace 100 may lack any ankle stays.

Referring again generally to FIGS. 1A-1G, the main body 102 of the ankle brace 100 also carries a strap assembly 130, which includes an adjustable stirrup assembly 132 and an adjustable securement assembly 134. The adjustable stirrup assembly 132 is coupled to the main body 102 and extends posteriorly to underlie the sole 24 of the wearer. The adjustable stirrup assembly 132 facilitates fitting the ankle brace 100 to the foot 10 of the wearer and providing varying degrees of foot support via the ankle brace 100.

The adjustable stirrup assembly 132 includes an inner stirrup 136 that is configured to underlie the sole 24 of the wearer. The inner stirrup 136 includes a first inner stirrup strap 138 and a second inner stirrup strap 140, which may be formed of fabrics, polymers, composites thereof, and the like. The first inner stirrup strap 138 is coupled to the first side portion 108 of the main body 102, and the second inner stirrup strap 140 is coupled to the second side portion 110 of the main body 102. In some embodiments, the first inner stirrup strap 138 includes a first, or superior, end portion 142 that is fixedly coupled to the main body 102 (for example, via stitching—not shown). The first inner stirrup strap 138 extends to a second, or inferior, end portion 144. The second inner stirrup strap 140 includes a first, or superior, end portion 146 that is fixedly coupled to the main body 102 (for example, via stitching—not shown). The second inner stirrup strap 140 extends to a second, or inferior, end portion 148, and the second end portions 144, 148 of the first inner stirrup strap 138 and the second inner stirrup strap 140 detachably couple to each other. In some embodiments and as illustrated, the second end portions 144, 148 of the first inner stirrup strap 138 and the second inner stirrup strap 140 detachably couple to each other via hook and loop fasteners (for example, the first inner stirrup strap 138 carries a plurality of hooks 150 (see FIG. 1D) and the second inner stirrup strap 140 carries a plurality of loops 152). In some embodiments and as illustrated, the second end portions 144, 148 of the first inner stirrup strap 138 and the second inner stirrup strap 140 are configured to detachably couple to each other under the sole 24 of the foot 10 of the wearer.

In other embodiments, the first inner stirrup strap 138 and/or the second inner stirrup strap 140 may take other forms or have other features. For example, the second end portions 144, 148 of the first inner stirrup strap 138 and the second inner stirrup strap 140 may detachably couple to each other in other manners, such as via clasps, buckles, laces, clamps, or the like. As another example, the second end portions 144, 148 of the first inner stirrup strap 138 and the second inner stirrup strap 140 may detachably couple to each other on the medial side 16 or the lateral side 14 of the foot 10. As another example, the first inner stirrup strap 138 and/or the second inner stirrup strap 140 may be integrally coupled to, or monolithically formed with, one or more layers of the main body 102. As yet another example, the first inner stirrup strap 138 and/or the second inner stirrup strap 140 may be detachably coupled to the main body 102 (for example, via hook and loop fasteners, clasps, buckles, laces, clamps, or the like).

The adjustable stirrup assembly 132 further includes an outer stirrup 154 that at least partially underlies the inner stirrup 136. In some embodiments and as illustrated, the outer stirrup 154 at least partially underlies both the first inner stirrup strap 138 and the second inner stirrup strap 140. The outer stirrup 154 includes a first outer stirrup strap 156 and a second outer stirrup strap 158, which may be formed of fabrics, polymers, composites thereof, and the like. In some embodiments, the first outer stirrup strap 156 and the second outer stirrup strap 158 are integrally coupled to, or monolithically formed with, each other and fixedly coupled to the first inner stirrup strap 138 or the second inner stirrup strap 140 (for example, via stitching—not shown). The first outer stirrup strap 156 extends superiorly from the inner stirrup 136 and along the first side portion 108 of the main body 102. The first outer stirrup strap 156 includes a superior end portion 160 that detachably couples to the first side portion 108 of the main body 102 (for example, via hook and loop fasteners, more specifically a plurality of hooks 162 carried by the first outer stirrup strap 156 (see FIG. 1E) and a plurality of loops 164 carried by the main body 102). The second outer stirrup strap 158 extends superiorly from the inner stirrup 136 and along the second side portion 110 of the main body 102. The second outer stirrup strap 158 includes a superior end portion 166 that detachably couples to the second side portion 110 of the main body 102 (for example, via hook and loop fasteners, more specifically a plurality of hooks 168 carried by the second outer stirrup strap 158 (see FIG. 1F) and the plurality of loops 164 carried by the main body 102).

In other embodiments, the first outer stirrup strap 156 and/or the second outer stirrup strap 158 may take other forms or have other features. For example, the first outer stirrup strap 156 and the second outer stirrup strap 158 may not be integrally coupled to each other, and the first outer stirrup strap 156 and the second outer stirrup strap 158 may be fixedly or detachably coupled to the inner stirrup 136. As another example, the superior end portions 160, 166 of the first outer stirrup strap 156 and the second outer stirrup strap 158 may detachably couple to the main body 102 other manners, such as via clasps, buckles, laces, clamps, or the like.

As briefly described above, the strap assembly 130 further includes the adjustable securement assembly 134. The adjustable securement assembly 134 is coupled to the main body 102 proximate the top portion 104. The adjustable securement assembly 134 facilitates fitting the ankle brace 100 to the foot 10 and calf 18 of the wearer.

The adjustable securement assembly 134 includes a bridge 170 disposed at the rear portion 114 of the main body 102. The bridge 170 is coupled to both the first side portion 108 of the main body 102 and the second side portion 110 of the main body 102. In some embodiments, the bridge 170 is fixedly coupled to both the first side portion 108 of the main body 102 and the second side portion 110 of the main body 102 (for example, via stitching). In other embodiments, the bridge 170 is detachably coupled to the first side portion 108 of the main body 102 and/or the second side portion 110 of the main body 102 or integrally coupled to the first side portion 108 of the main body 102 and/or the second side portion 110 of the main body 102. The bridge 170 may be formed of fabrics, polymers, composites thereof, and the like.

The adjustable securement assembly 134 further includes a first securement strap 172 and a second securement strap 174, which may be formed of fabrics, polymers, composites thereof, and the like. The first securement strap 172 and the second securement strap 174 are disposed posteriorly relative to the bridge 170. Stated another way, the bridge 170 is configured to be disposed between the leg of the wearer and the first securement strap 172 and the second securement strap 174. The first securement strap 172 is coupled to the first side portion 108 of the main body 102, and the second securement strap 174 is coupled to the second side portion 110 of the main body 102. In some embodiments, the first securement strap 172 includes a first, or lateral, end portion 176 that is fixedly coupled to the main body 102 (for example, via stitching—not shown). The first securement strap 172 extends to a second, or medial, end portion 178. The second securement strap 174 includes a first, or medial, end portion 180 (see FIG. 1C) that is fixedly coupled to the main body 102 (for example, via stitching—not shown). The second securement strap 174 extends to a second, or lateral, end portion 182, and the second end portions 178, 182 of the first securement strap 172 and the second securement strap 174 detachably couple to each other. In some embodiments and as illustrated, the second end portions 178, 182 of the first securement strap 172 and the second securement strap 174 detachably couple to each other via hook and loop fasteners (for example, the first securement strap 172 carries a plurality of hooks 184 (see FIG. 1C) and the second securement strap 174 carries a plurality of loops 186).

In other embodiments, the first securement strap 172 and/or the second securement strap 174 may take other forms or have other features. For example, the second end portions 178, 182 of the first securement strap 172 and the second securement strap 174 may detachably couple to each other in other manners, such as via clasps, buckles, laces, clamps, or the like. As another example, the first securement strap 172 and/or the second securement strap 174 may be integrally coupled to, or monolithically formed with, one or more layers of the main body 102. As another example, the first securement strap 172 and/or the second securement strap 174 may be detachably coupled to the main body 102 (for example, via hook and loop fasteners, clasps, buckles, laces, clamps, or the like). As yet another example, the first securement strap 172, the second securement strap 174, and the bridge 170 may be disposed on the front portion 112 of the main body 102.

Figure 1G:
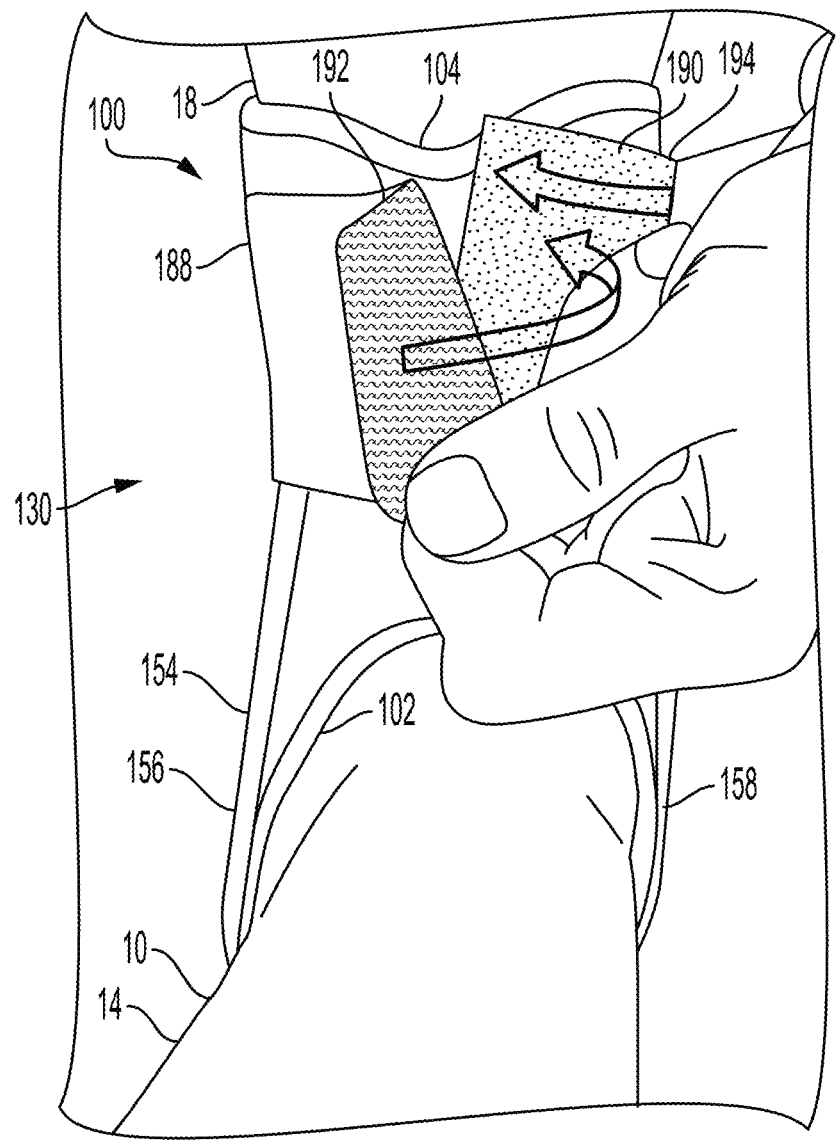
FIG. 1G is a front perspective view of the ankle brace of FIG. 1A being secured to the foot of the wearer.

The adjustable securement assembly 134 further includes a first upper wrapping strap 188 and a second upper wrapping strap 190 to secure the ankle brace 100 to the foot 10 of the wearer. The first upper wrapping strap 188 and the second upper wrapping strap 190 extend from the first securement strap 172, around the main body 102 adjacent the top opening 116, and the first upper wrapping strap 188 overlies and is detachably coupled to the second upper wrapping strap 190. In some embodiments, the first upper wrapping strap 188 and the second upper wrapping strap 190 are monolithically formed with each other. In some embodiments, the first upper wrapping strap 188 and the second upper wrapping strap 190 fixedly couple to the first securement strap 172 (for example, via stitching—not shown). In some embodiments and as illustrated, the first upper wrapping strap 188 and the second upper wrapping strap 190 detachably couple to each other via hook and loop fasteners (for example and as shown in FIG. 1G, the first upper wrapping strap 188 carries a plurality of hooks 192 and the second upper wrapping strap 190 carries a plurality of loops 194). In other embodiments, the first upper wrapping strap 188 and the second upper wrapping strap 190 detachably couple to each other in other manners, such as via clasps, buckles, laces, clamps, or the like.

Ankle braces according to some embodiments of the present disclosure may include additional or different features, components, shapes, dimensions, and/or characteristics than the ankle brace 100 described above. For example, in some embodiments strap assemblies of ankle braces include different components and/or features. An exemplary embodiment of such an ankle brace is described below.

Figure 2A:
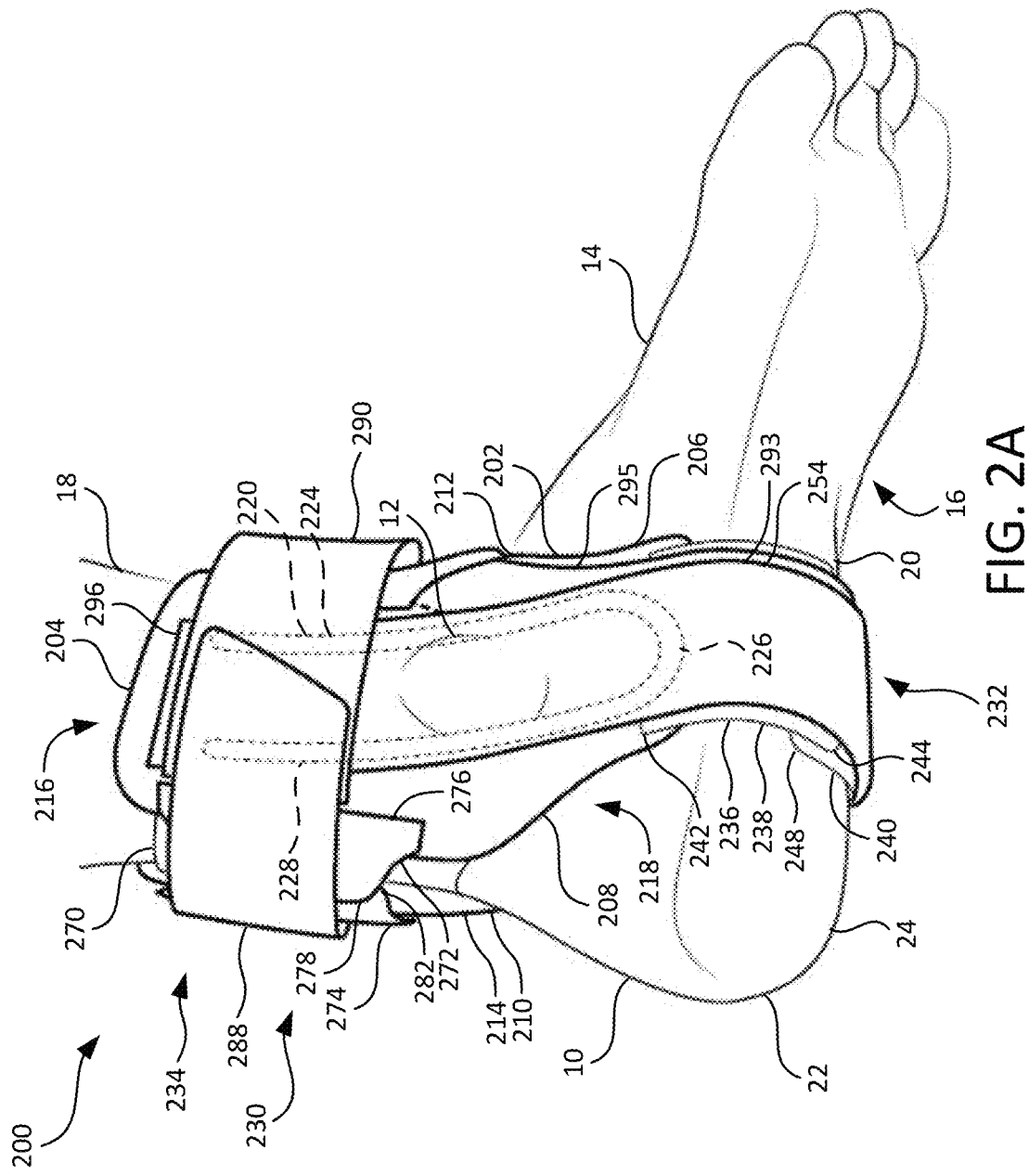
FIG. 2A is a side perspective view of an ankle brace according to another embodiment of the present disclosure being worn on a foot of a wearer.
Figure 2B:
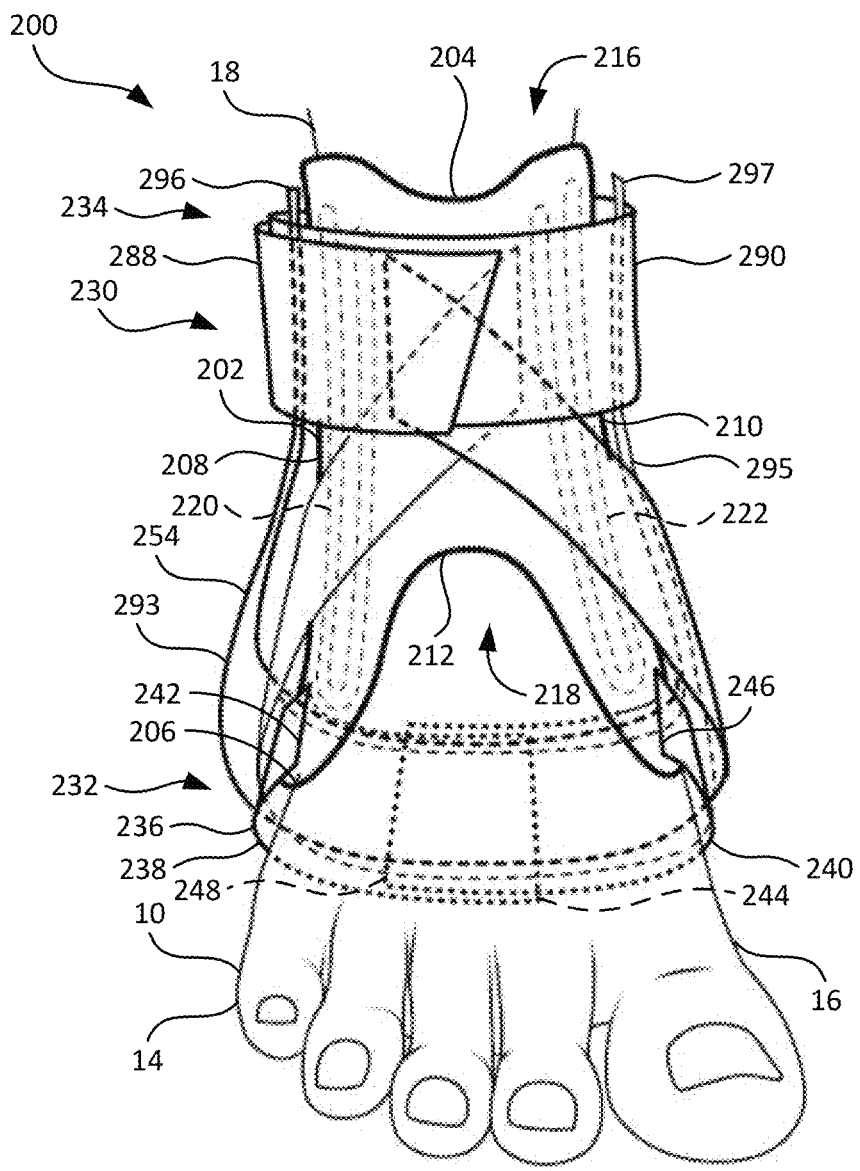
FIG. 2B is a front perspective view of the ankle brace of FIG. 2A being worn on the foot of the wearer.
Figure 2C:
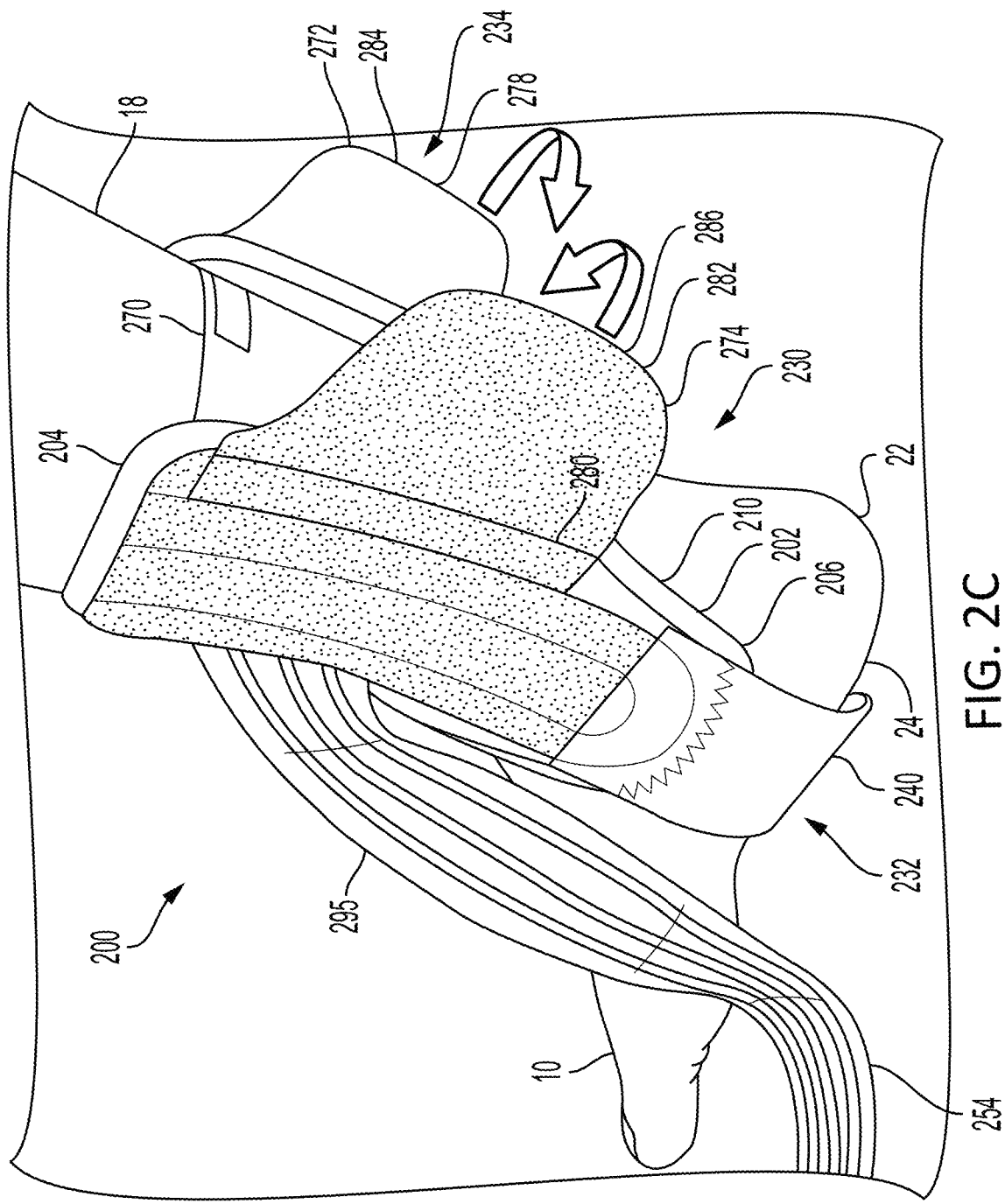
FIG. 2C is a side perspective view of the ankle brace of FIG. 2A being secured to the foot of the wearer.
Figure 2D:
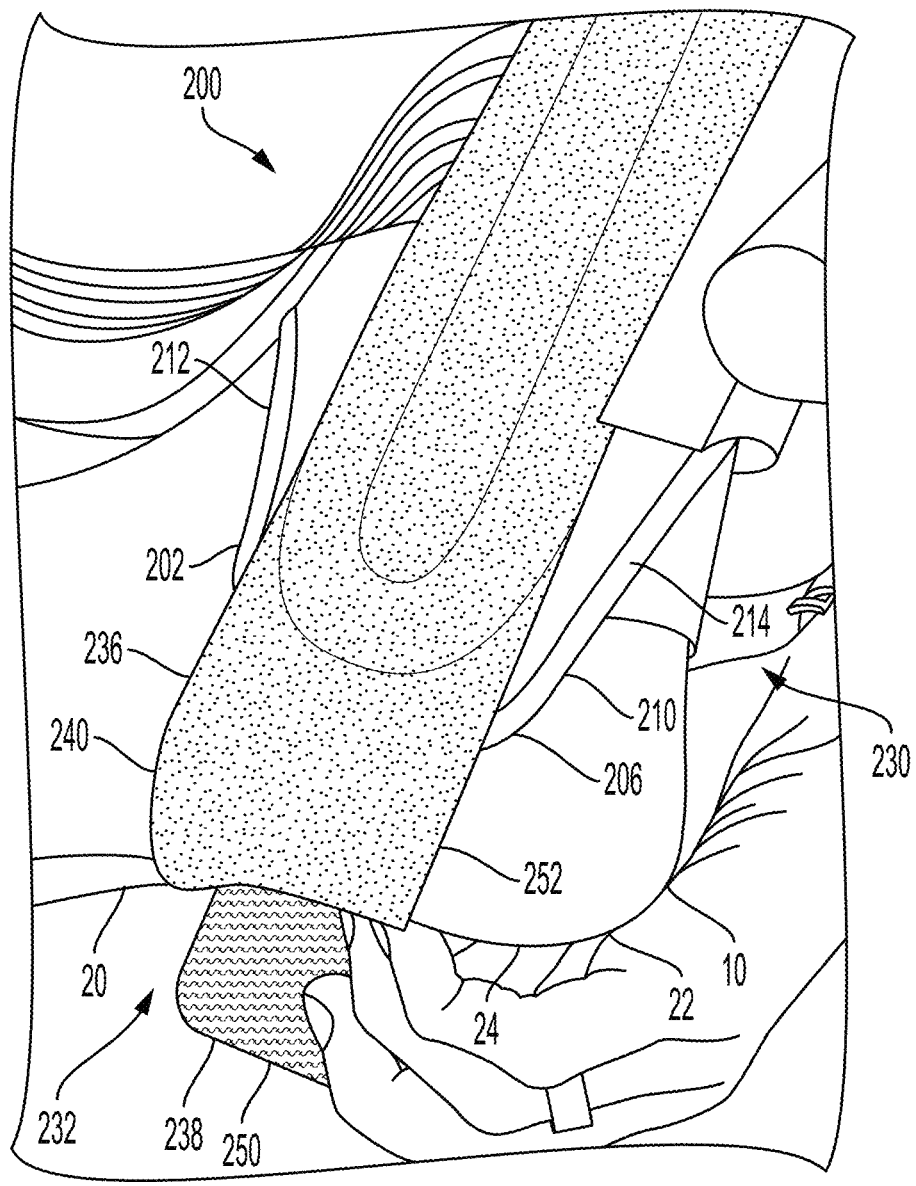
FIG. 2D is another side perspective view of the ankle brace of FIG. 2A being secured to the foot of the wearer.
Figure 2F:
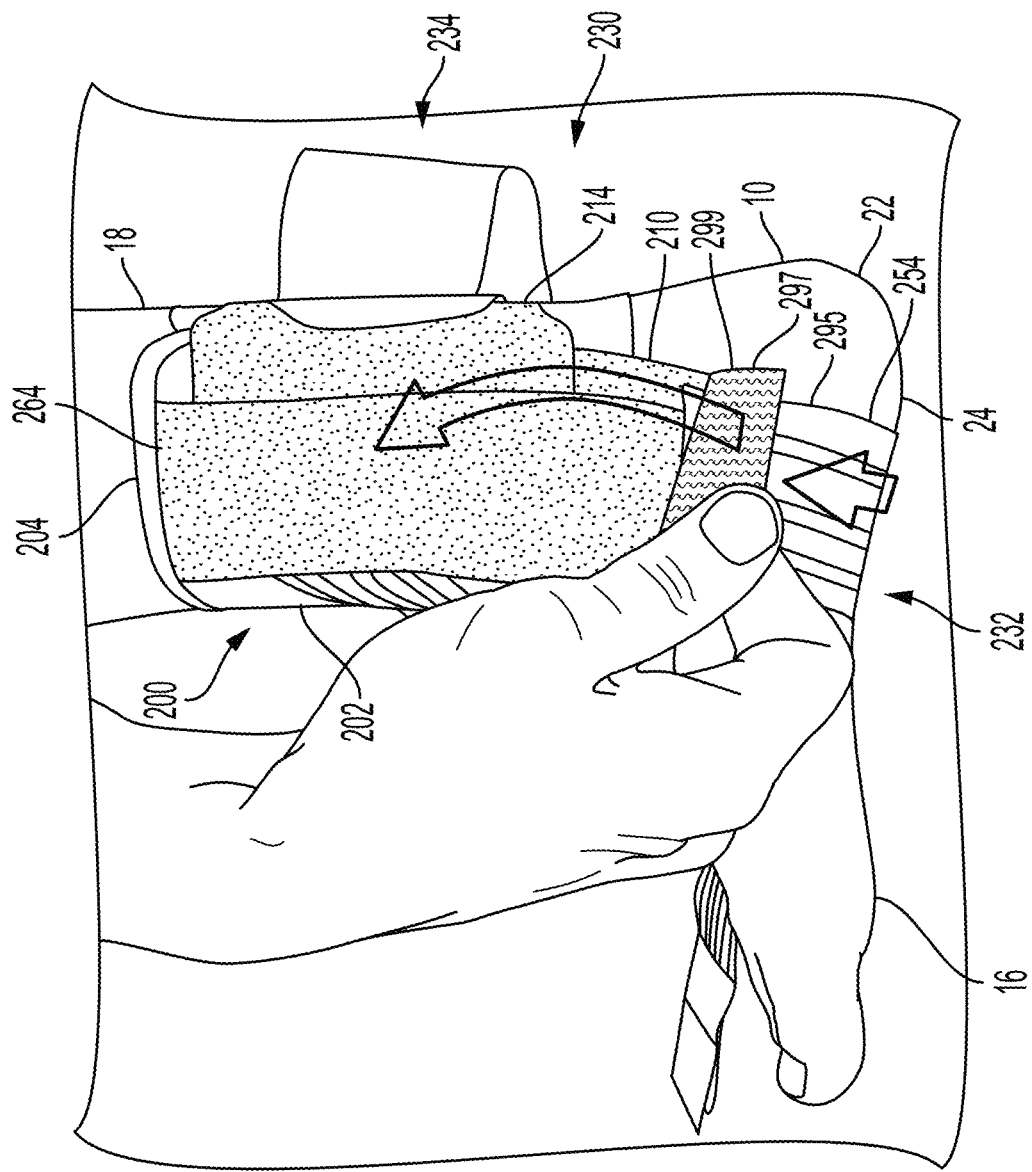
FIG. 2F is another side perspective view of the ankle brace of FIG. 2A being secured to the foot of the wearer.
Figure 2G:
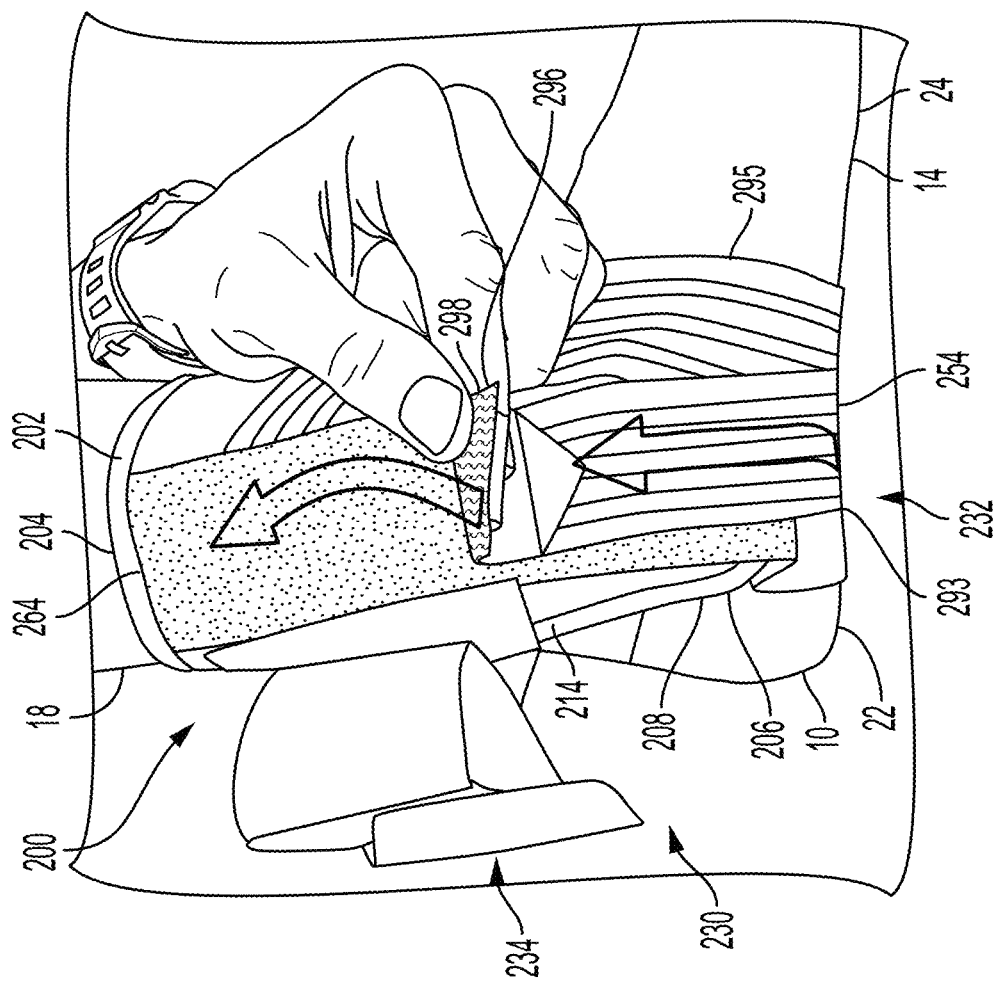
FIG. 2G is another side perspective view of the ankle brace of FIG. 2A being secured to the foot of the wearer.
Figure 2H:
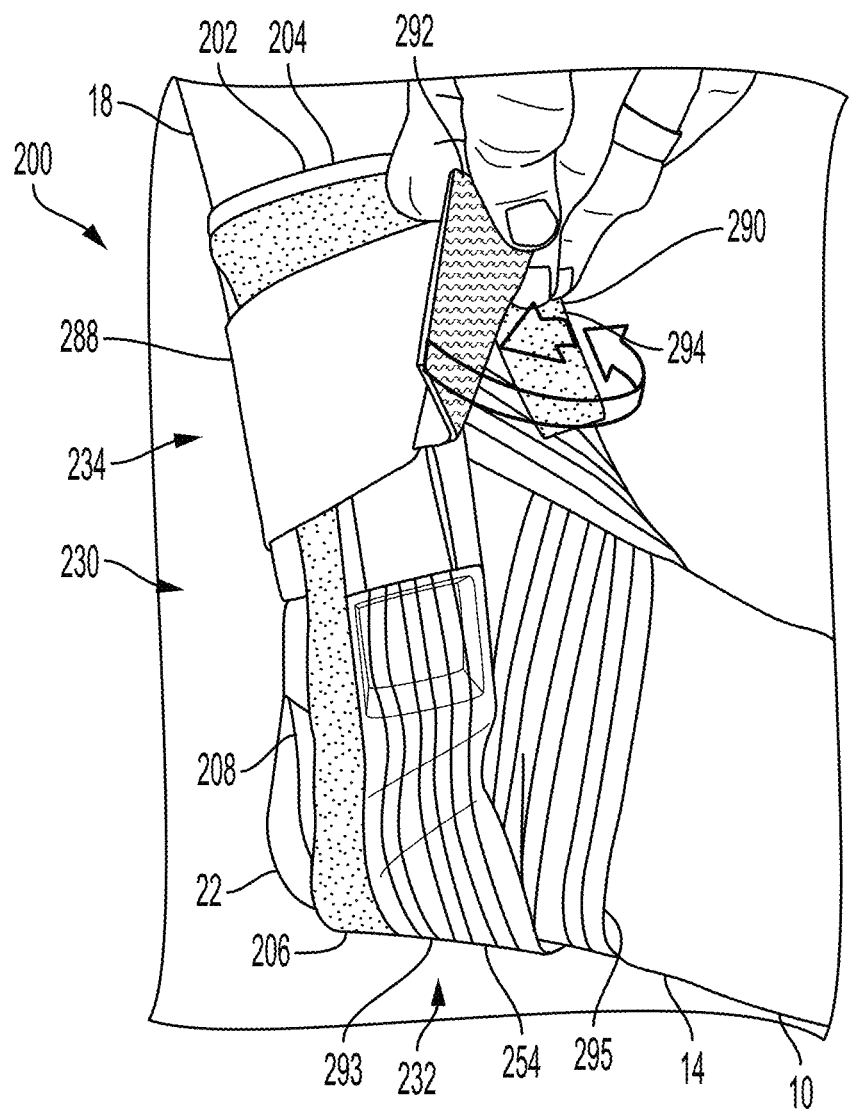
FIG. 2H is yet another side perspective view of the ankle brace of FIG. 2A being secured to the foot of the wearer.

FIGS. 2A and 2B illustrate an ankle brace 200 according to another embodiment of the present disclosure being worn on the foot 10 of a wearer. FIGS. 2C-2G illustrate the ankle brace 200 being secured to the foot 10 of the wearer. The ankle brace 200 includes a main body 202 that is configured to receive the foot 10 of the wearer, including the ankle 12. The main body 202 generally includes similar components and features compared to the main body 102, and in the drawings similar components and features are represented by the same reference numbers increased by 100 (that is, the main body 202 includes a top portion 204, a bottom portion 206, a first side portion 208, a second side portion 210, a front portion 212, a rear portion 214, and so forth). The main body 202 of the ankle brace 200 also carries a strap assembly 230, which includes an adjustable stirrup assembly 232 and an adjustable securement assembly 234. The adjustable securement assembly 234 generally includes similar components and features compared to the adjustable securement assembly 234, and in the drawings similar components and features are represented by the same reference numbers increased by 100 (that is, the adjustable securement assembly 234 includes a first securement strap 272, a second securement strap 274, and so forth). The adjustable stirrup assembly 232 generally includes similar components and features compared to the adjustable stirrup assembly 232, and in the drawings similar components and features are represented by the same reference numbers increased by 100 (that is, the adjustable stirrup assembly 232 includes a first inner stirrup strap 238, a second inner stirrup strap 240, and so forth). However, the adjustable stirrup assembly 232 includes an outer stirrup 254 that has crossing first and second crossing outer stirrup straps 293, 295 (also referred to as a first crossing outer stirrup strap 293 and a second crossing outer stirrup strap 295) instead of the first outer stirrup strap 156 and the second outer stirrup strap 158, respectively.

The first crossing outer stirrup strap 293 and the second crossing outer stirrup strap 295 may be formed of fabrics, polymers, composites thereof, and the like. The first crossing outer stirrup strap 293 and the second crossing outer stirrup strap 295 fixedly couple to the front portion 212 of the main body 202 (for example, via stitching—not shown). The first crossing outer stirrup strap 293 and the second crossing outer stirrup strap 295 extend from and cross each other on the front portion 212 of the main body 202, extend inferiorly along the second side portion 210 and the first side portion 208 of the main body 202, respectively, extend under the sole 24 and cross each other again, and then extend superiorly along the first side portion 208 and the second side portion 210 of the main body 202, respectively, to superior end portions 296, 297, respectively. The superior end 296, 297 portions detachably couple to the main body 202 (for example, via hook and loop fasteners, more specifically a plurality of hooks 298, 299 carried by the first crossing outer stirrup strap 293 and the second crossing outer stirrup strap 295, respectively, (see FIGS. 2F and 2G) and the plurality of loops 264 carried by the main body 202).

In other embodiments, the first crossing outer stirrup strap 293 and/or the second crossing outer stirrup strap 295 may take other forms or have other features. For example, the first crossing outer stirrup strap 293 and the second crossing outer stirrup strap 295 may be detachably coupled to the main body 202 at the front portion 212. As another example, the superior end portions 296, 297 of the first crossing outer stirrup strap 293 and the second crossing outer stirrup strap 295 may detachably couple to the main body 202 other manners, such as via clasps, buckles, laces, clamps, or the like.

Various other modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. An ankle brace comprising:
   a main body configured to receive a foot of a wearer, the main body having a first side portion and a second side portion opposite the first side portion;
   an adjustable stirrup assembly coupled to the main body, the adjustable stirrup assembly comprising:
   an inner stirrup configured to underlie the sole of the foot of the wearer, the inner stirrup comprising:
   a first inner stirrup strap coupled to the first side portion of the main body;

a second inner stirrup strap coupled to the second side portion of the main body, the second inner stirrup strap detachably coupling to the first inner stirrup strap;

an outer stirrup at least partially underlying the inner stirrup; and an adjustable securement assembly coupled to the main body, the adjustable securement assembly comprising:

a first securement strap coupled to the first side portion of the main body;

a second securement strap coupled to the second side portion of the main body, the second securement strap configured to detachably couple to the first securement strap posteriorly of the Achilles tendon of the wearer; and a bridge fixedly coupled to the first side portion of the main body and the second side portion of the main body, the bridge being configured to contact the skin disposed posteriorly of the Achilles tendon of the wearer and be disposed between the Achilles tendon of the wearer and the first securement strap and the second securement strap.

2. The ankle brace of claim 1, wherein the adjustable securement assembly further comprises a first upper wrapping strap.

3. The ankle brace of claim 2, wherein the adjustable securement assembly further comprises a second upper wrapping strap, the second upper wrapping strap being detachably coupled to the first upper wrapping strap.

4. The ankle brace of claim 1, wherein the first inner stirrup strap comprises a first end portion fixedly coupled to the first side portion of the main body and a second end portion, the second inner stirrup strap comprises a first end portion fixedly coupled to the second side portion of the main body and a second end portion, the second end portion of the second inner stirrup strap detachably coupling to the second end portion of the first inner stirrup strap.

5. The ankle brace of claim 1, wherein the outer stirrup at least partially underlies both of the first inner stirrup strap and the second inner stirrup strap.

6. The ankle brace of claim 1, wherein the first inner stirrup strap and the second inner stirrup strap are configured to detachably couple to each other under the sole of the foot of the wearer.

7. The ankle brace of claim 1, further comprising:

a plurality of loops carried by the first inner stirrup strap; and a plurality of hooks carried by the second inner stirrup strap, the plurality of hooks detachably coupling to the plurality of loops to detachably couple the second inner stirrup strap to the first inner stirrup strap.

8. The ankle brace of claim 1, wherein the outer stirrup comprises a first crossing outer stirrup strap that detachably couples to the first side portion of the main body and a second crossing outer stirrup strap that detachably couples to the second side portion of the main body.

9. An ankle brace comprising:

a main body configured to receive a foot of a wearer, the main body having a first side portion and a second side portion opposite the first side portion;

a stirrup coupled to the main body and configured to underlie the sole of the foot of the wearer, the stirrup comprising:

a first stirrup strap coupled to the first side portion of the main body;

a second stirrup strap coupled to the second side portion of the main body, the second stirrup strap detachably coupling to the first stirrup strap;

an adjustable securement assembly coupled to the main body, the adjustable securement assembly comprising:

a first securement strap coupled to the first side portion of the main body; and a second securement strap coupled to the second side portion of the main body, the second securement strap configured to detachably couple to the first securement strap posteriorly of the Achilles tendon of the wearer; and a bridge fixedly coupled to the first side portion of the main body and the second side portion of the main body, the bridge being configured to contact the skin disposed posteriorly of the Achilles tendon of the wearer and be disposed between the Achilles tendon of the wearer and the first securement strap and the second securement strap.

10. The ankle brace of claim 9, further comprising:

a plurality of hooks carried by the first securement strap; and a plurality of loops carried by the second securement strap, the plurality of loops detachably coupling to the plurality of hooks to detachably couple the second securement strap to the first securement strap.

11. The ankle brace of claim 9, wherein the first stirrup strap comprises a first end portion fixedly coupled to the first side portion of the main body and a second end portion, the second stirrup strap comprises a first end portion fixedly coupled to the second side portion of the main body and a second end portion, the second end portion of the second stirrup strap detachably coupling to the second end portion of the first stirrup strap.

12. The ankle brace of claim 9, wherein the first stirrup strap and the second stirrup strap are configured to detachably couple to each other under the sole of the foot of the wearer.

13. The ankle brace of claim 9, further comprising:

a plurality of hooks carried by the first stirrup strap; and a plurality of loops carried by the second stirrup strap, the plurality of loops detachably coupling to the plurality of hooks to detachably couple the second stirrup strap to the first stirrup strap.

14. The ankle brace of claim 9, wherein the adjustable securement assembly further comprises an upper wrapping strap.

* * * * *